US006334074B1

(12) United States Patent
Spertell

(10) Patent No.: US 6,334,074 B1
(45) Date of Patent: Dec. 25, 2001

(54) MICROWAVE APPLICATOR FOR THERAPEUTIC USES

(75) Inventor: Robert B. Spertell, Northridge, CA (US)

(73) Assignee: Microwave Medical Corp., Simi Valley, CA (US)

( * ) Notice: Subject to any disclaimer, the term of this patent is extended or adjusted under 35 U.S.C. 154(b) by 0 days.

(21) Appl. No.: 09/474,969

(22) Filed: Dec. 29, 1999

Related U.S. Application Data

(63) Continuation of application No. 08/904,175, filed on Jul. 31, 1997, now Pat. No. 6,104,959.

(51) Int. Cl.[7] ........................................................ A61F 2/00
(52) U.S. Cl. .................... 607/101; 607/102; 607/154; 606/9; 606/31
(58) Field of Search ................................. 607/100–102, 607/115, 154, 156; 606/27–34, 41–42, 9–13; 128/898

(56) References Cited

U.S. PATENT DOCUMENTS 5,148,814 * 9/1992 Kikuchi et al. ...................... 607/101
6,104,959 * 8/2000 Spertell .............................. 607/101

* cited by examiner

Primary Examiner—John P. Lacyk
Assistant Examiner—Ryan Carter
(74) Attorney, Agent, or Firm—Raymond A. Bogucki

(57) ABSTRACT

A hand held applicator for delivery of microwave energy to skin surfaces is provided that is compact, easily manipulated, precisely positionable and secure against malfunction. Microwave energy of a chosen frequency is supplied for a given duration at a predetermined energy level, via one or more waveguides having a distal end section that is dielectrically loaded and matched to skin impedance. Positioning indicia may be disposed on a single use end cap adjacent the emitter end of the applicator to permit easy visualization by the surgeon or technician. Coolant, such as a pressurized gas refrigerant, is supplied in a burst to the skin surface via an interior solenoid controlled valve. The microwave energy pulse is initiated by control circuits after the effective delivery of coolant is sensed. The initiation of the cycle can be effected by actuation of a switch, movement of the applicator against the skin, or by tracking the movement of the applicator from one position to another. Further, two or more microwave energy emitters may be disposed in the same housing in a compact fashion, and arranged to fire serially at the chosen target locations.

28 Claims, 7 Drawing Sheets

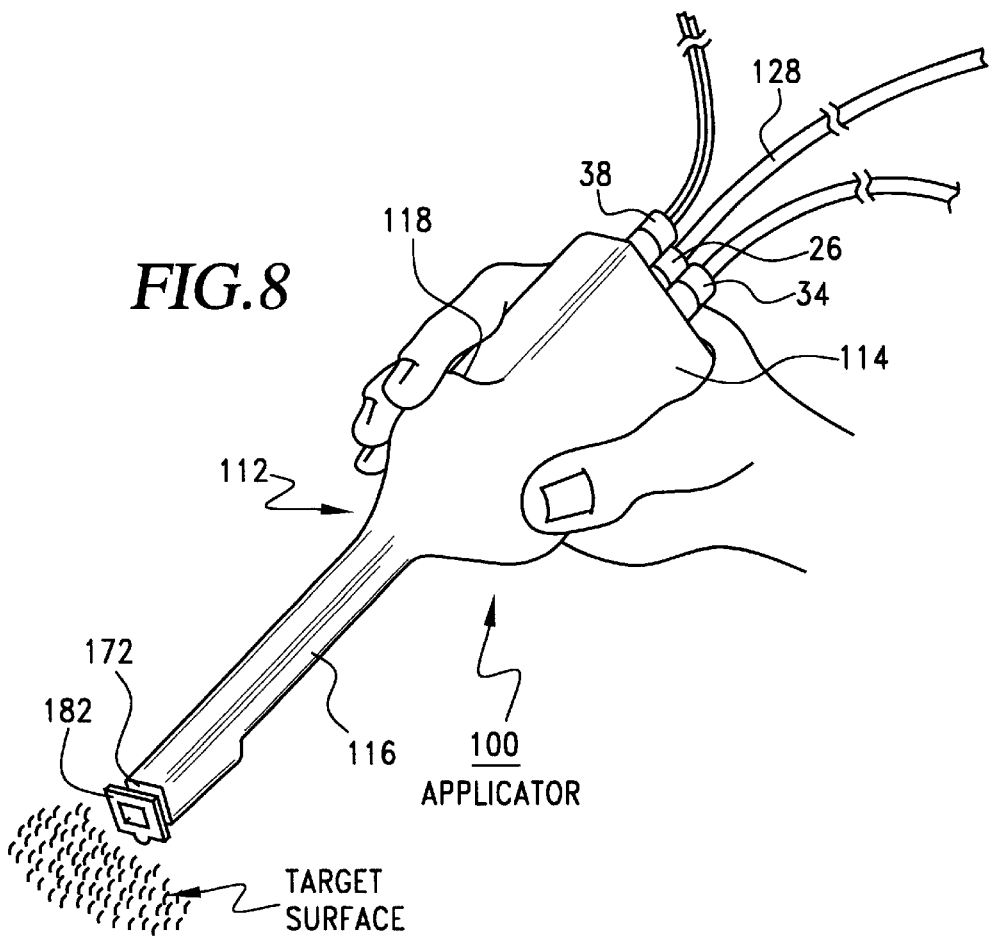
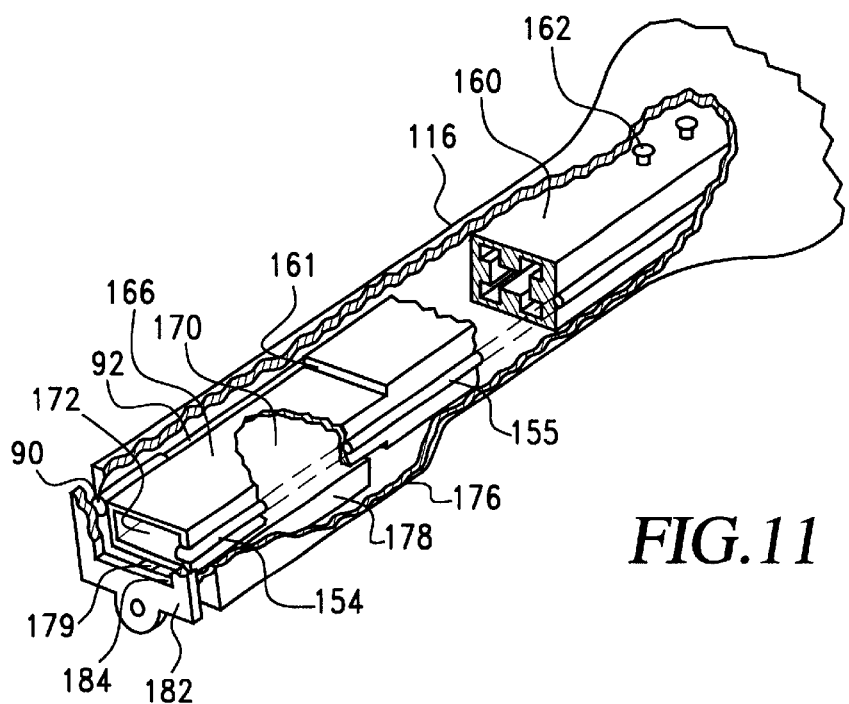

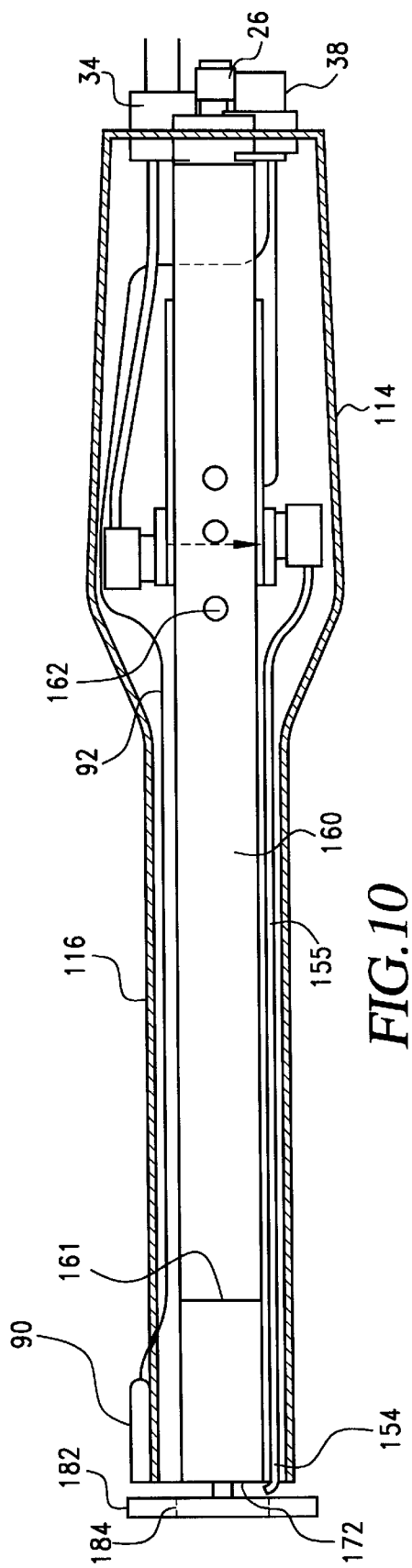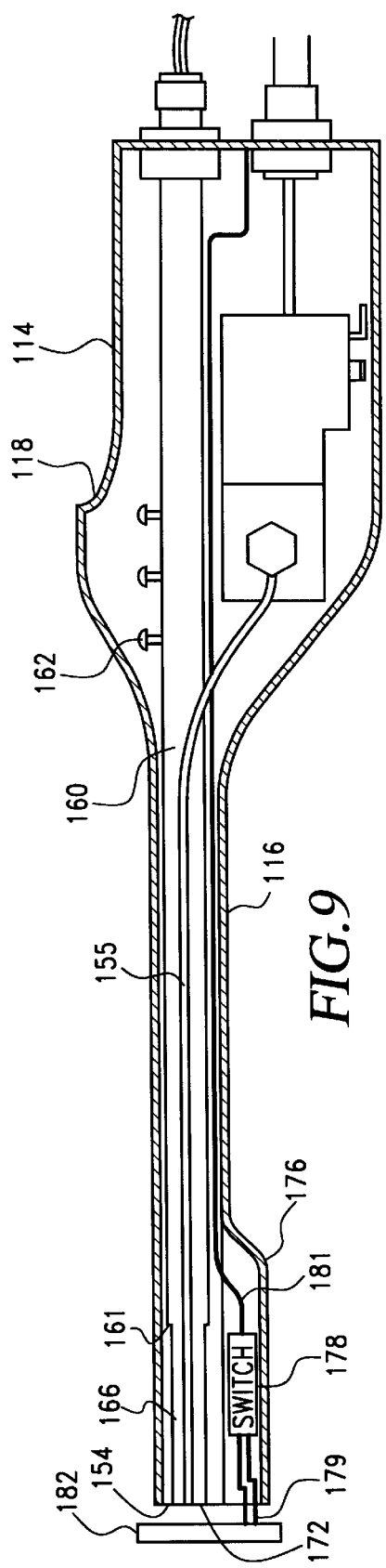

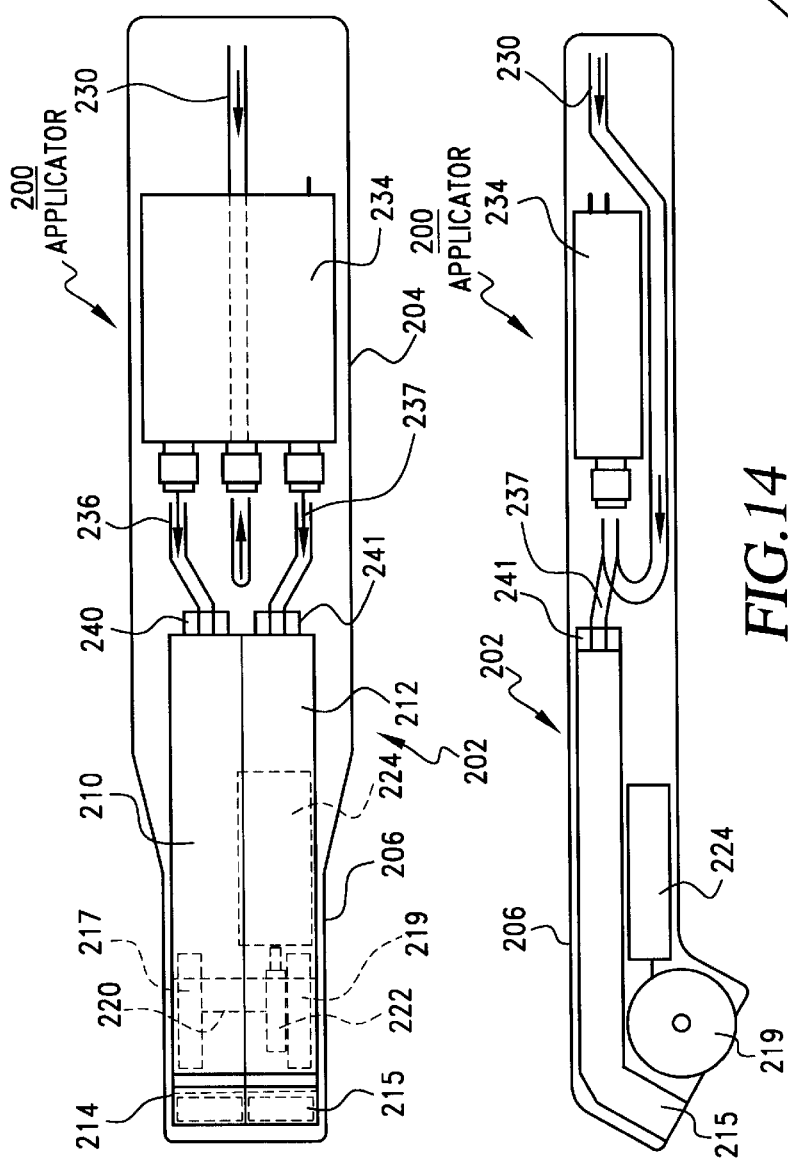
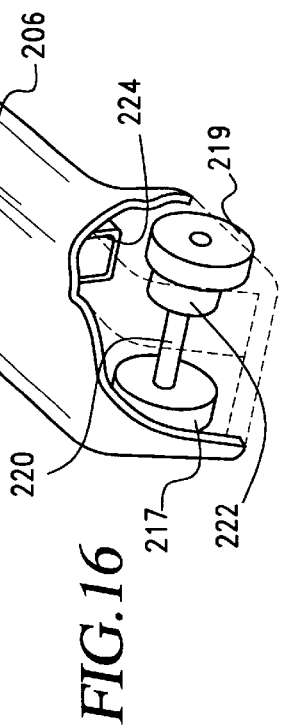
FIG. 15
FIG. 14
FIG. 16

MICROWAVE APPLICATOR FOR THERAPEUTIC USES

This application is a continuation of U.S. application Ser. No. 08/904,175, filed Jul. 31, 1997, now U.S. Pat. No. 6,104,959.

FIELD OF THE INVENTION

This invention relates to devices and methods for delivering microwave energy to localized areas of the surface of the human body, and more particularly to handheld energy applicators which are compact, readily manipulable, and capable of delivering microwave energy at desired energy doses to discrete target areas of the body.

BACKGROUND OF THE INVENTION

It has been shown, in the above-referenced co-pending application, that microwave energy can effectively be used to create beneficial histological changes in subdermal, dermal and superficial features, such as blood vessels, skin, wrinkles and hair in the human body. By properly balancing the intensity and total energy applied to a limited surface area, the microwave energy penetrates to a chosen depth and interacts in a manner to effect the desired changes without harm or trauma to the patient. For example, a subdermal skin condition, commonly referred to as spider veins, (telangiectasia) is treatable by energy dosages which penetrate through the dermis to heat localized subdermal areas to above a critical temperature, such as in excess of 60° C. The localized temperature increase causes inflammation of vessel walls, subsequently blocking blood flow and impelling the creation of new blood flow paths, thus eliminating the appearance of spider veins. Other subdermal conditions such as varicose veins, which involve larger, deep tissue vessels, can also be treated because of the penetrating character of the microwave energy. Similarly, collagen tissue and adipose deposits may be treated by microwaves using the same principles. The aspect being treated may also be primarily a surface condition, such as wrinkles, stretch marks, cellulite, warts or dermal lesions.

Depilation is a related application in which microwave energy has been found to be particularly useful. For effective depilation the energy penetrates to reach follicular matrices and papillae, attacking the base of hair follicles and minimizing hair regrowth.

Microwave wavelengths are selected such that the wave energy preferentially interacts with the targeted tissues, such as blood or vessel walls, to enhance the localized effects of the treatment. Energy doses are kept within a range suitable for both safety and patient comfort.

Laser energy, which is widely used for similar purposes, is at much shorter wavelengths which penetrate organic matter much less effectively, and heat by absorption in superficial tissues or hair, but only when the target has the needed light responsive characteristics. Heat is then transferred from the impinged surface into a subdermal or deep tissue area to effect a histological change. The laser energy can be intensified, in order to penetrate more deeply, but still is significantly attenuated and also is much more likely to cause skin burns. For depilation treatments, laser energy must impinge upon light absorptive pigmentation in exposed hair and rely on the side effect of heat transfer to attack the follicular matrices. Light reflection and light rejection at less densely pigmented tissues and follicles diminishes the amount of useful energy, thereby making laser treatment inefficient for such targets. Skin resurfacing treatments, based upon radiative effects on collagen and adipose tissues, for example, are also more efficient where wave energy reaches the target tissue with little attenuation.

In these treatment systems, as described in the above referenced application, discrete surface targets are selected and radiated with microwave energy until a target feature or area peripheral to the target area has been excited with energy of chosen intensity and duration. Since a wide beam delivering heating energy to a broad area could undesirably affect non-target regions, energy application should be with a device having a small transmitting end which delivers a narrow energy beam. Because the concentration of electromagnetic wave energy is highest immediately adjacent the transmitting source, the skin surface adjacent the source is cooled so as to minimize overheating, discomfort and trauma. Various expedients for this purpose include use of a cooled, thermally conductive member in contact with the skin, cooling of the skin by expanding a pressurized coolant directed against the skin, and pre-cooling the skin with a frigid element or liquid. It is essential that such sources be used in timed relation to the application of wave energy from the applicator, and that the cooling not interfere with or diminish the applied energy. Moreover, the thermal transfer dynamics should preferably be complementary to the microwave energy application, in terms of time of delivery, thermal gradient in the tissues, and the temperature levels that are maintained.

Further, the energy applicator should not impair viewing by the doctor or technician, or occlude the target area, but should preferably permit clear visualization along with precise placement of the applicator at the target surface. The cross-sectional area of the transmitting end of the device, therefore, must be relatively small, and appropriately sized in relation to the target area to be treated. The minimum cross-sectional emitter area is determined by the wavelength chosen and the overall size and mass also have to be suitable for manual handling of the unit. The power level of the energy (watts) and the energy concentration (joules/cm$^2$) that are to be used must also be accommodated in the design of the device. The prior application referenced above has disclosed how the cross-sectional area of the emitter end of the device can be reduced by incorporating dielectric materials. The device must not only be compact, but it should be ergonomically designed for easiest placement and actuation, so that a relatively large target area can be covered by successive applications without redundancy. In addition, the dangers of erroneous energization, excessive exposure, and improper sequencing should be minimized in ways that free the operator from responsibilities for safeguards to the extent possible.

SUMMARY OF THE INVENTION

Handheld energy applicators in accordance with the present invention are advantageously configured for one hand operation, and contain all operative elements within a housing have a convenient handle that extends or curves into an extension of smaller cross-section which incorporates a transmitting aperture or emitter at its distal end. The distal end is configured to be precisely placeable relative to a target area, and also includes integrated means for delivering a cooling medium at the target area until a temperature level is attained that allows safe delivery of a microwave pulse via the aperture. The energy level and duration of the applied microwave energy for a preferred wavelength are chosen for the treatment desired.

In one example of an applicator in accordance with the invention, wave energy from a source is fed to the proximal end of the applicator via a flexible coaxial line, and launched within the applicator into one or more double ridged waveguides extending along the slim distal extension. The ridged waveguide occupies most of the extension and reduces the cross-sectional area needed for a chosen wavelength. The distal end of the extension comprises a short converging tapered or stepped length which preferably includes a dielectric that further reduces the form factor and provides an impedance substantially matching that of the target area. The transmitting aperture is established at a predetermined close spacing to the skin surface at the target area by a terminal spacer which contacts the surface and also includes indicia for precise placement of the applicator relative to a target area to be treated. A coolant line extends along the waveguide within the applicator housing from a pressurized source through a signal-operated solenoid-controlled valve to terminate in an open nozzle section at the distal end. The cycle is initiated by directing expanded coolant across the target area until a selected temperature threshold is attained, then initiating a microwave pulse of selected energy and duration.

The complete microwave energy applicator system comprises a self-contained manual unit coupled by flexible lines to a pulse source of microwave energy, a pressurized coolant source, a signal source for actuating the valve and control circuits to control timing and adjust power level and pulse duration of the microwave energy. A temperature sensor is incorporated at the distal end of the applicator to sense that coolant is being effectively delivered before the microwave energy is applied. The switch for the operator may be located at a fingertip position or be responsive to an end-mounted mechanism that can be pressed against the skin to start. Indicator lights on the housing are visible to the operator to denote readiness status and error conditions.

In an example of an applicator in accordance with the invention, designed for small size and ergonomic advantages, the housing comprises a generally rounded base for retention in the hand between the thumb and forefinger. The base smoothly curves into a smaller diameter end section with a narrowed waist region conforming to the thumb and forefingers and terminating in a distal end at which the transmitting aperture of a waveguide projects. A spacer element, preferably disposable, fits removably over the transmitting aperture and is shaped to provide a predetermined gap, between a skin target area and the end of the waveguide, which confines and directs the coolant within a limited volume having a vent at one side. The coolant line extends from the posterior end of the housing through the base portion, where flow of a gas refrigerant is controlled by a solenoid-operated valve. A photodetection device in the coolant path may be utilized to determine if liquid is present in the refrigerant since this could adversely affect cooling. At the distal end of the housing, a nozzle directs coolant within the limited volume across the face of the transmitting aperture, tangentially along the target area, within the spacer. The spacer includes an egress or venting port which offers low impedance to flow and unrestricted egress of the refrigerant to a deflecting shield which directs the coolant away from the skin. The operator can observe the indicator lights on the top of the base portion of the housing, so as to be assured that a new cycle can be initiated after a prior one is completed. The initiating switch is located conveniently to the tip of a forefinger on the top of the distal end section. Compactness is aided also by a coaxial feedline within the base from its posterior end to a transition coupling into the double ridged waveguide. Another feature provided by the spacer is the inclusion of one or more protruding positional markers, visible to an operator and enabling easy placement of the emitter at a target area.

In another example of a device in accordance with the invention, the principal length of the interior waveguide comprises a double ridged waveguide section leading from the proximal end of the housing through the intermediate region, into a step transition joining to a reduced area end cross-section that is dielectric loaded. The distal end includes both a coolant outlet nozzle and a spaced apart thermistor open to the adjacent gap between the transmitting aperture and the skin surface. In this example, placement is facilitated by a target area framing element that is movable axially through a small distance to engage the start switch. When in that position the framing element provides the desired gap between the skin surface and the emitter aperture, at the time of cycle initiation. A solenoid actuated valve straddles the waveguide in mid-region of the housing, so that a coolant line from the pressurized source to the valve is connected through the valve to an output coolant line extending along the waveguide to the distal end. The housing has a bulbous handle sized and configured to be held in the palm with the fingers extending distally to engage the narrow elongated end with a pencil-type grip. The housing exterior has a smooth, curved transition section that merges down into the elongated distal end and keeps the emitter end and indicia in full sight.

In yet another example of a device in accordance with the invention, two or more emitter units are positioned to be adjacent in side-by-side or above and below relation to the applicator housing, so that a larger target area can be covered at each position by applying energy pulses to two or more adjacent areas. For the double applicator, two parallel and adjacent double ridged waveguides proximate to the distal end are fed by a single switch within the housing that receives microwave energy from the pulse source. This may be a single pole double throw RF switch, having a single inlet port, for input from a coaxial waveguide along the central axis and with parallel outputs feeding to individual coaxial waveguides coupled separately to the double ridged waveguides. For convenient handling of the unit and delivery of the energy in a direction normal to the skin, the ends of the waveguides are angled, as through a 60° angle, at an elbow region before the adjacent emitter apertures. A user can thus hold this slightly larger unit conveniently, at an acute angle to the surface of the skin, for easiest placement and application of energy. With adjacent emitter apertures, the switch alternates pulses between the emitters at each target position, in timed relation to applied coolant pulses. After energy delivery at a first site, the applicator can then be moved orthogonally relative to the paired emitters to the next position. To provide automatic placement of the transmitting apertures relative to target areas, a tracking wheel device that rolls on the skin surface measures the incremental distance needed to reach the next adjacent target area. A trigger switch responsive to the tracker wheel movement indicates to the user that the unit is in position to begin the next sequence of coolant and microwave pulses, or it automatically triggers the sequence itself.

Other features of devices in accordance with the invention reside in the distal end spacer and the method of cooling the surface of the target area. The spacer, which is essentially a single use disposable device but can be resterilized, is a low cost unitary molded element that removably attaches about the emitter aperture at the distal end of the applicator. In position, it encompasses the emitter but has an opening at the skin surface side that is coextensive and aligned with the emitter aperture. The spacer is dimensioned to maintain the emitter aperture at a predetermined small gap from the skin surface, while defining an interior volume adjacent the skin surface that is open only at one side, used for venting. Coolant gas flowing across the targeted surface from one side of the emitter aperture is thus confined within the volume until it reaches the opposite side of the spacer, where it is vented away from the skin surface, but encounters minimal impedance.

The cooling method utilizes the cooling effect of an expanded gas, such as an environmentally approved refrigerant derived from an ambient temperature pressurized source (e.g., a small pressurized vessel). A burst of gas is begun prior to application of microwave energy, and cools the skin surface convectively until a desired threshold temperature is sensed at the venting side by a temperature sensitive device. On sensing the lowering of temperature below the threshold the microwave pulse is initiated, and the coolant flow can be discontinued, at the value although this need not be precise, and flow continues until lines are cleared. The skin surface temperature is reduced, typically in the range of 10–250° C., but with a total open time of the solenoid in the 10–25 MS (milliseconds) range. The cooling penetrates to the upper part of the dermis. The method has been shown to be highly effective in limiting surface irritation and adverse effects from microwave applications.

BRIEF DESCRIPTION OF THE DRAWINGS

A better understanding of the invention may be had by reference to the following description, taken in conjunction with the accompanying drawings, in which:

FIG. 8 is a perspective view of a different example of an applicator in accordance with the invention;

FIG. 9 is side sectional view of the applicator of FIG. 8;

FIG. 10 is a top sectional view of the applicator of FIGS. 8 and 9;

FIG. 11 is a fragmentary perspective view, partially broken away, showing further details of the distal end of the arrangement of FIGS. 8–10;

FIG. 14 is a side sectional view of an example of an applicator in accordance with the invention utilizing two side by side waveguides;

FIG. 15 is a plan sectional view of the applicator of FIG. 14, showing further details thereof; and FIG. 16 is an enlarged perspective view of a fragment of the arrangement of FIGS. 14 and 15, showing further details of the device for measuring the spacing between target positions.

DETAILED DESCRIPTION OF THE INVENTION

Figure 1:
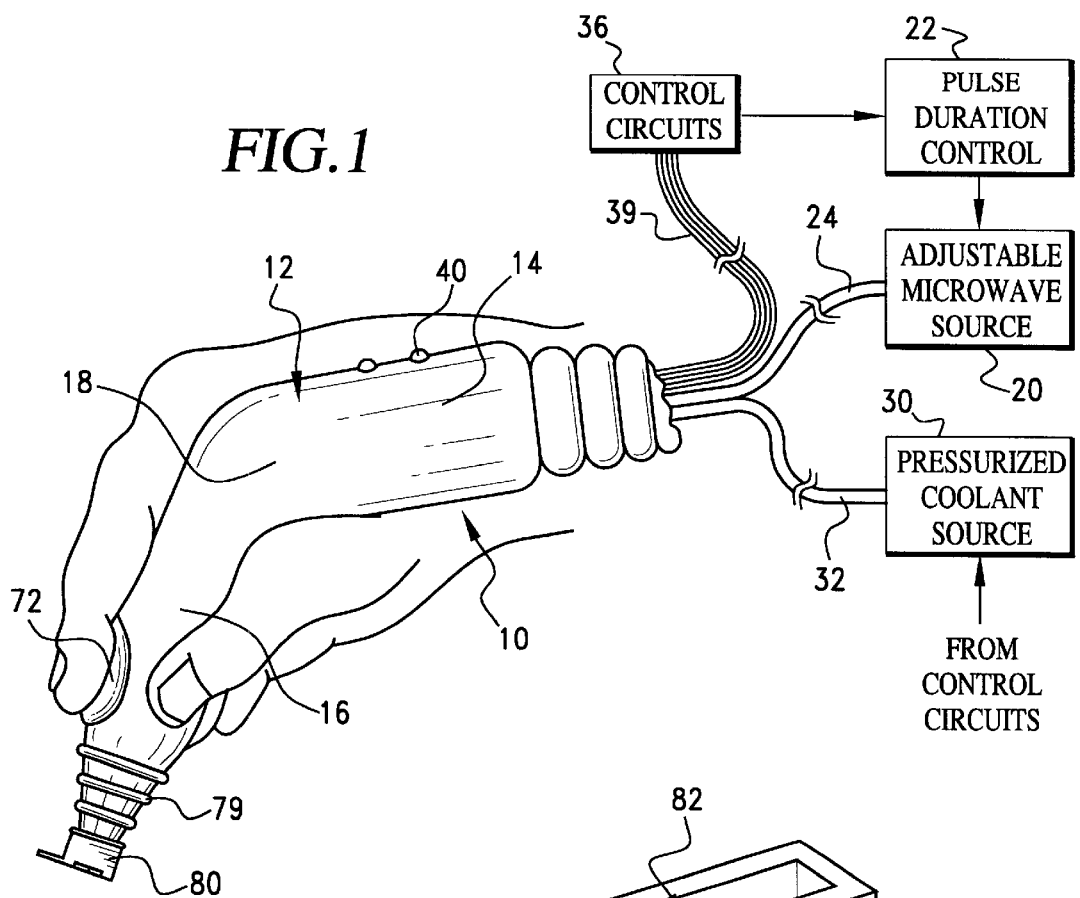
FIG. 1 is a combined block and perspective view of an example of an energy applicator in accordance with the invention having a single waveguide and emitter aperture.

FIGS. 1–7 depict an applicator 10 in accordance with the invention including a slim line housing 12 having a streamlined, base portion 14 at the proximal end, and an elongated, narrower distal portion 16 at a substantial angle, but slightly less than 90°. A curved intermediate region merges the bulbous base 14 to the elongated distal portion 16 in a smooth, continuous fashion. The distal portion 16 has a narrowed but smooth merging waist region 18 that provides a natural ergonomic reference for gripping the applicator in pencil-type fashion, with the bulbous base 14 between the thumb and index finger and the forefinger extending distally along the elongated portion 16, for easiest manipulation. The housing 12 is preferably of a lightweight, insulative material such as molded plastic.

The applicator 10 receives microwave energy as pulses of chosen duration from a microwave energy source 20 (FIG. 1 only) which is adjustable in power and has a selected frequency range from about 2 to 20 GHz, as described in the above referenced application. Preferably, the source is in the range of about 14 GHz for best matching to a receptive tissue or constituent, such as blood, vascular structure, or hair follicles. A pulse duration control 22 is also coupled to the microwave energy source 20, which is typically a magnetron, traveling wave tube or other source. Selection of power and duration determines the total energy delivered in a pulse, which is preferably in the range of about 20–30 joules/cm$^2$ for depilation, and usually within 20–28 joules/cm$^2$. The microwave signal is fed from the source 20 via a flexible coaxial feed line 24 to a microwave port 26 at the proximal end of the housing 12.

The applicator system also includes a pressurized gas coolant source 30, which for cost, convenience and ease of use will typically be a pressurized refrigerant bottle having a nominal pressure of about 50–250 psi, typically about 80 psi. Further, the refrigerant itself is preferably an environmentally non-deleterious compound, such as HFC 134A, or 1,1,1,2 tetrafluorethane, for example. A flexible conduit 32 capable of withstanding the input pressure couples the source 30 to a coolant port 34 at the proximal end of the housing 12.

Control circuits 36 for responding to the appropriate inputs provide signals to the applicator 10 and the pulse duration control 22 to operate the active elements in properly timed relation.

The proximal end of the housing 12 also includes a signal coupler port 38 through which electrical lines 39 (FIG. 1) coupled to the control circuits 36 are conducted into and out of the interior of the applicator housing 12. A pair of indicator lights 40 are disposed on the proximal end of the housing 12, to indicate various operative conditions, such as power, readiness to operate, and delay interval. The sensors and logic for actuating these indicator lights 40 are conventional, and therefore not depicted in this example.

Figure 6:
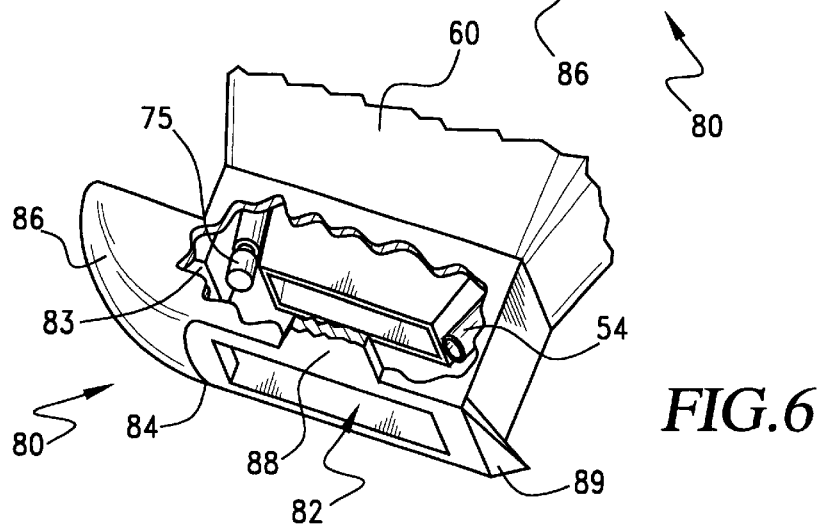
FIG. 6 is a fragmentary perspective view, partially broken away, of an attached spacer device.
Figure 2:
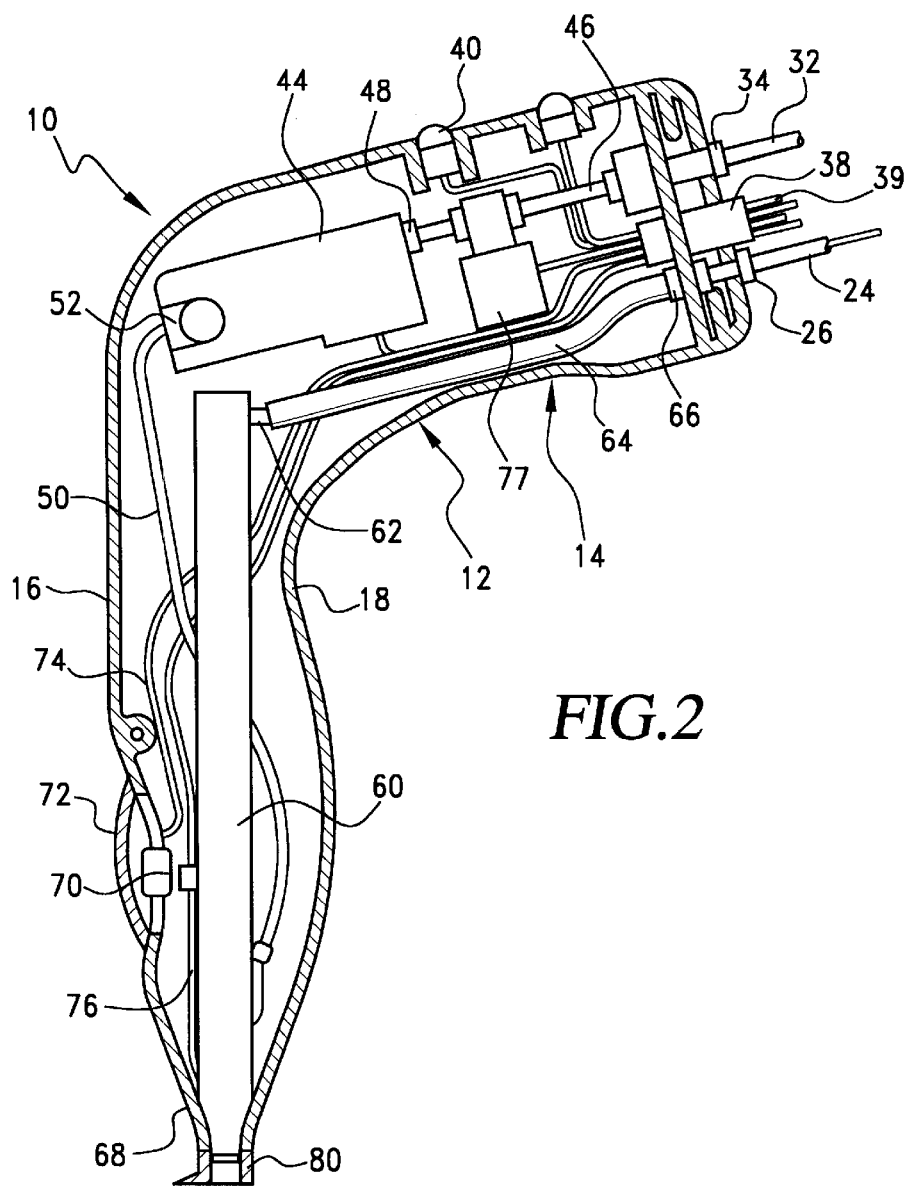
FIG. 2 is a side sectional view of the arrangement of FIG. 1, showing further details thereof.
Figure 7:
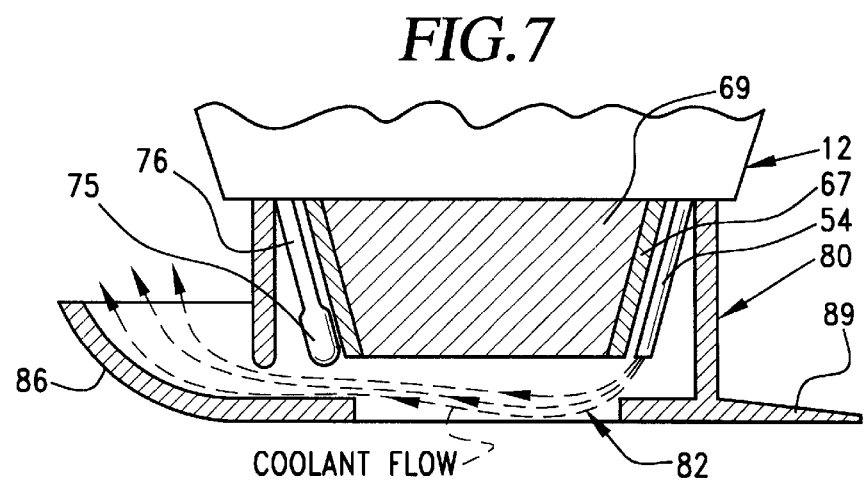
FIG. 7 is a side cross-sectional view of the installed spacer of FIG. 6, showing the coolant flow therein.
Figure 3:
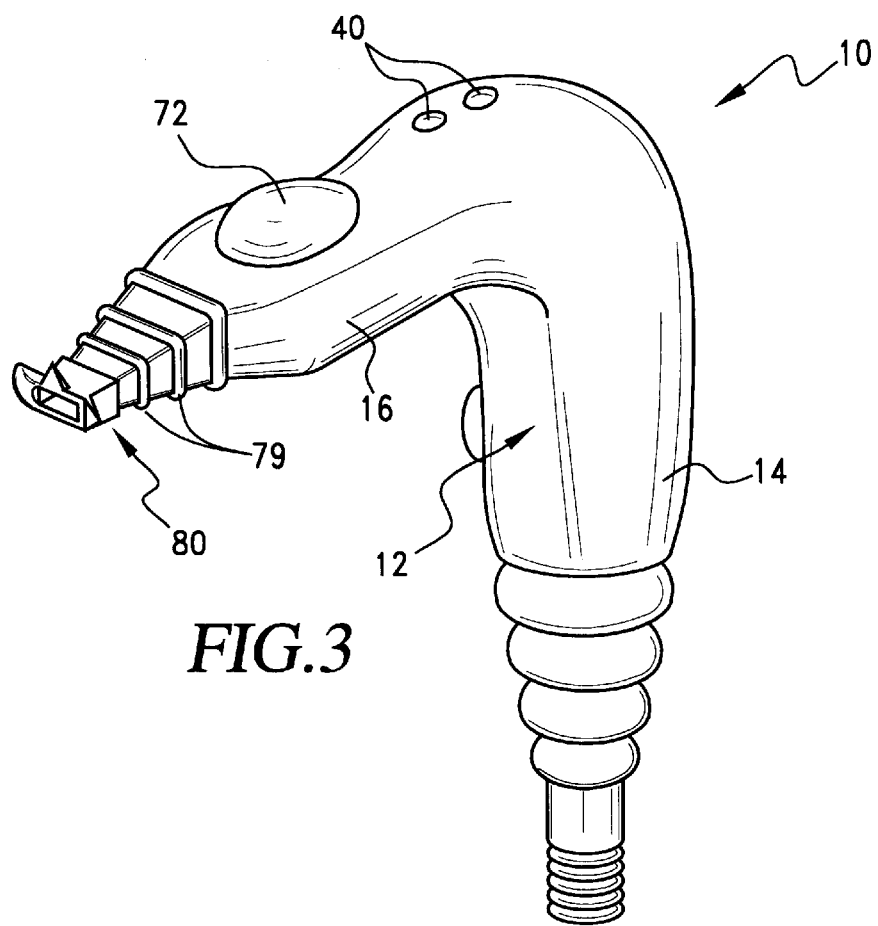
FIGS. 3 is different perspective view of the arrangement of FIGS. 1 and 2.
Figure 4:
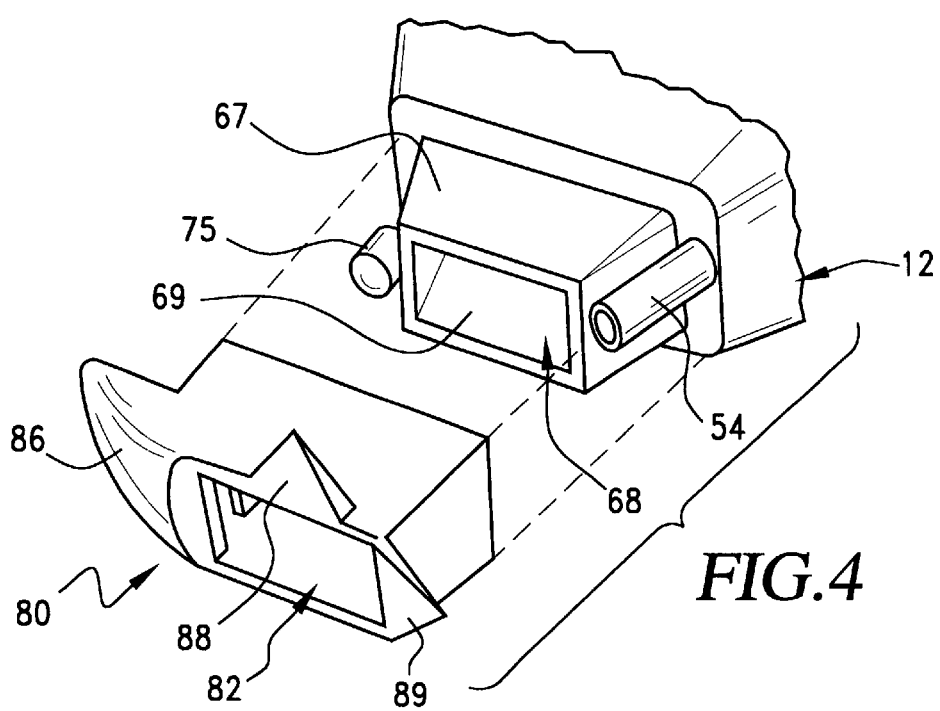
FIG. 4 is an exploded fragmentary view, of the distal end of the applicator of FIGS. 1–3 showing a refrigerant nozzle and end spacer that are employed in the arrangement of FIGS. 1–3.
Figure 13:
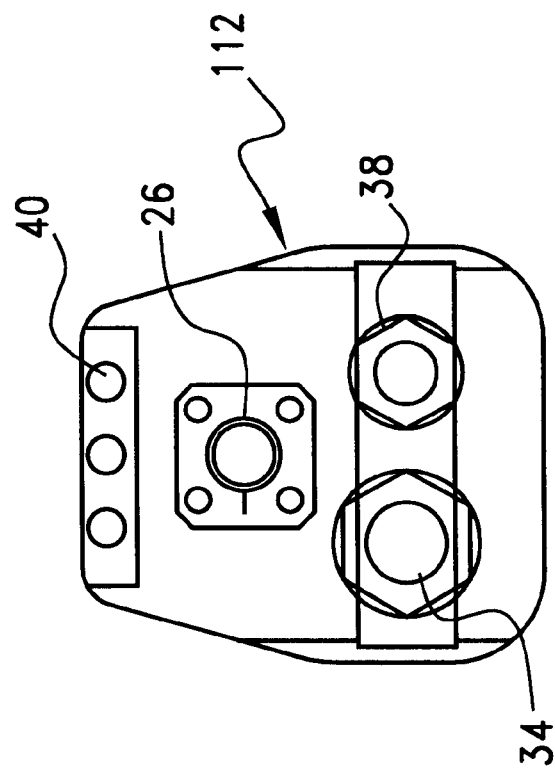
FIG. 13 is an end view of the posterior end of the applicator of FIGS. 8–10.
Figure 12:
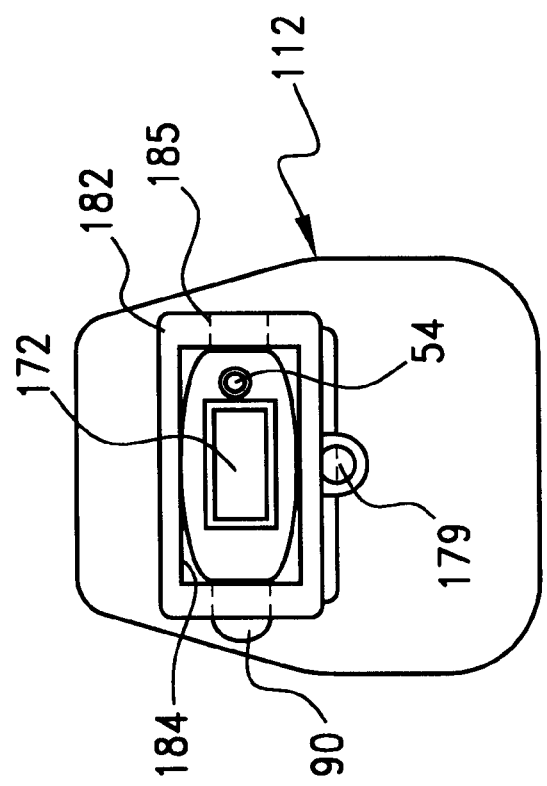
FIG. 12 is an end view of the distal end of the applicator of FIGS. 8–10.

Within the base 14 of the housing 12, a solenoid-controlled valve 44 for gating the gas coolant flow is mounted with its body along the length of the housing and with the valve portion transversely straddling the central axis of the housing 12, as best seen in FIG. 2. An input coolant conduit 46 from the coolant port 34 extends along one side of the housing 12 to an input port 48 on the same side of the solenoid-controlled valve 44. At the opposite side of the valve portion of the solenoid-controlled valve 44, an output coolant conduit 50 extends along the housing 12, from an output port 52 on the valve to the distal end of the housing 12. The end of the output coolant conduit 50 is open, defining a jet nozzle 54, which in this example is elliptical in cross-section, to facilitate flow across the target area from one side of the distal end of the housing 12. Alternatively, the jet nozzle can be disposed in various orientations, including transverse to the skin surface that is to be engaged, or it can branch, prior to the end section, into two or more jet nozzles, for example. The arrangement shown, which is best seen in FIGS. 4 and 6, is however more direct and of proven effectiveness.

The central structure within the applicator housing 12, for microwave transmission, as best seen in FIG. 2, comprises a double ridged waveguide 60 extending along the central region of the distal elongated portion 16, and receiving energy from a coax to waveguide transition 62 coupled to a coaxial waveguide 64 that leads to a connector 66, such as an SMA connector at the proximal end of the housing 12. The double ridged waveguide 60 reduces the cross-sectional dimension needed for the chosen wavelength, and leads to a terminating transition section 67 which converges to an emitter aperture 68 of approximately 6 mm×4 mm size. The transition section 67 is loaded with a dielectric 69 which permits reduction of the emitter aperture 68 to that size. Referring again to FIGS. 1 and 3 in addition to FIG. 2, an initiator switch 70 is directly under a flexible control button 72 which is convenient to the forefinger of an operator holding the applicator 10 in a normal position. An electrical line 74 which carries signals indicating the switch 70 status is coupled back along the waveguide structure 60 to the signal coupler port 38. A thermistor 75 is positioned at the distal end of the housing 12, to sense the approximate temperature at the distal end of the applicator 10. The thermistor 75 indicates the effect of coolant that has been jetted from the nozzle 54 and when the system is ready to operate. A signal line 76 (FIG. 2) from the thermistor 75 returns to the proximal end of the housing 12 and then to the control circuits 36, which control the initiation and sequencing of the coolant and microwave power cycles. The input coolant line 46 includes a photodetector 77 for sensing the presence of liquid in the coolant at that point. At the narrow end of the distal portion of the housing 12, O rings 79 are set in grooves to enable the operator to grip the extreme end if desired.

Figure 5:
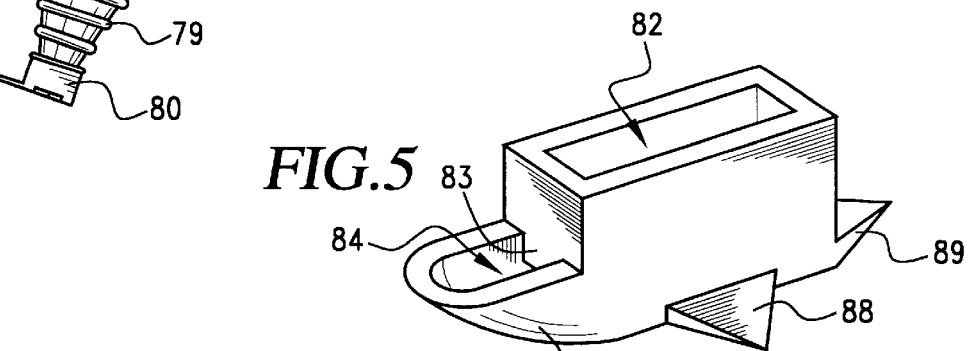
FIG. 5 is a different perspective view of the end spacer of FIG. 4.

The applicator 10 also includes a spacer 80 for detachably mounting on the protruding portion of the waveguide 60 at its distal end. The spacer 80 is preferably disposable, so that it can be replaced on a single use basis by fitting it frictionally on to the end of the waveguide. As seen in FIGS. 5 and 6, the spacer 80 defines a boundary about the transmitting aperture 68, confining an interior volume 82 and providing a precise axial separation, here about 0.020 inches of the aperture 68 from the skin surface. This enables the applicator 10 to be held against the skin of a subject while precisely maintaining the chosen distance between the transmitting aperture and the subject to allow for cooling while preventing skin damage. The jet nozzle 54 for refrigerant is positioned at one side to feed into this interior volume 82, which has an internal wall 83 defining an egress port 84 (FIG. 5) on the opposite side from the nozzle 54. Thus the expanding gas refrigerant flows across the surface of the skin to be irradiated, between the transmitting aperture 68 and the skin, and passes through the port 84 in a lateral direction. A curved or angled deflector wall 86 forming a part of the spacer 80 directs the gases that move through the port 84 away from the skin so that cooling is limited to the area that is receiving microwave energy. The outer periphery of the spacer 80 here includes two visible indicator markers 88, 89 each in the form of a tapered projection or fin. In this example, two orthogonally disposed locator fins 88, 89 each centered as to a different side of the transmitting aperture 68 are shown. More or fewer may be used, depending on the particular procedure and the nature of preparatory target markings placed on the skin.

Referring again to FIGS. 1–7, this applicator 10 is compact, and held in one hand in a natural manner. Additionally, the indicator markers 88, 89 on the spacer 80 enable correct placement at the target area since they can be seen by the user regardless of the angle of the view. Typically, removable marks will be placed on the skin of the patient prior to initiation of the procedure, and the markers 88, 89 can be placed relative to these for successive applications.

The base 14 is held, pencil style, against the palm of the hand and between the fingers and points in the direction of the elongated end 16, which facilitates instinctive placement at the target area on the patient's skin. Here is it assumed, for purposes of illustration only, that the therapeutic procedure involved is depilation, so that the wattage and duration are selected to give an appropriate amount of joules/cm$^2$, using the adjustable microwave source 20 and pulse duration control 22 as operated by the control circuits 30. Suitable results are obtained with total dosage levels of the order of 20–28 joules/cm$^2$ for 10–50 MS delivered to the applicator. In a specific practical example for depilation the dosage level was about 24–25 joules/cm$^2$ delivered in a 25–30 MS pulse with a surface temperature drop, caused by the coolant, of about 12° C. Initially, however, coolant flow is used to assure that the skin temperature will be lowered by pre-cooling. The pressurized coolant source 30 constantly pressurizes the line 32 and the internal coupling up to the input port 48 of the solenoid control valve 44. Checking the indicator lights 40 (FIG. 1) the operator has verification that the sequence can be initiated, after correctly placing the spacing marker fins 88, 89 at the distal end of the applicator 10 against a chosen area, usually premarked with lines or dots on the skin surface. Such placement assures that the transmitting aperture 68 at the distal end is precisely in position. By pressing the control button 72 on the applicator 10, the initiator switch 70 is actuated, signaling the control circuits 36 to commence the controlled cycle. To begin, the solenoid control valve 44 is actuated to open the coolant line 50 from the output port 52 on the valve 44, thus directing a flow of expanding coolant from the jet nozzle 54 along the skin across the target area. The characteristic flow pattern, best seen in FIG. 7, chills the skin surface by convection as the expanding refrigerant gas flows within the limited internal spacer volume 82. The gas moves without restriction under the barrier 83, through the vent opening 84, and then is deflected away from the skin surface at the deflector 86. Because the internal volume 82 defines a precise and small separation between the emitter aperture 68 and the skin surface, and because outward side flow is blocked, the skin surface is efficiently cooled. The coolant pulse is usually from 10–25 MS long, and a temperature drop of about 10–25° C. is typically sufficient at the skin surface, although the thermal gradient extends partially into the dermis. At the end of the coolant pulse, when the valve is again closed, some flow continues until the lines are clear.

The thermistor 75 signal detecting a reduced temperature is returned to the control circuits 36, until a threshold is reached indicating sufficient cooling at the site. If no reduction is sensed the microwave energy is not delivered. In normal operation, however, within less than 20 milliseconds, the pulse duration control 22 is triggered by detection of a temperature below the threshold. The triggering actuates the microwave source 20 to deliver the energy pulse for effecting microwave penetration and histological change in the target region. Under the conditions stated the desired changes are not accompanied by irritation or trauma.

In a second example of an applicator 100 in accordance with the invention, referring now to FIGS. 8–13, the applicator housing 112 has a slim line base 114 with a projection 118 providing a reference for an operator who holds base 114 in his hand. The base merges toward an elongated distal end 116 and terminates at an emitter or transmitting aperture as previously described. However, the interior waveguide 160 (FIGS. 9–11) comprises a double ridged waveguide coupled at an SMA connector 26 (as in FIGS. 4 and 2) to an input feed coaxial waveguide 128 coupled to the posterior end of the housing 112. In the distal portion 116 of the housing 112, the rectangular waveguide 160 joins at a step transition 161 to a reduced height end section 166 that is filled with a dielectric material 170 (FIG. 11 only) comprising a loading element that extends to the emitter aperture 172 on the waveguide 160. Tuning screws 162 provided in the double ridged waveguide 160 enable electrical matching of waveguide impedance. A jet nozzle 154 for gas coolant extends from a coolant line 155 as previously described.

Adjacent its distal end, the housing 112 has a streamlined, enlarged side extension 176 which incorporates a small switch 178 from which an actuator finger 179 extends distally out from the distal end of the housing 112. The electrical line 181 (FIGS. 9 and 10) which carries signals indicating the switch 178 status is coupled back along the waveguide structure 160 to a signal or coupler port 38. A target framing element 182 transverse to the longitudinal axis of the waveguide structure 160 is at the same time parallel to the skin surface to be engaged. The framing element 182 defines an interior opening 184 (FIGS. 10–12) that encompasses and borders the emitter aperture 172 of the waveguide structure 160, and may also include guide markings 185 visible to the operator of the applicator 100 to precisely indicate the boundaries of the emitter aperture 172. The switch 178 may be manually operated. Alternatively, however, as shown here, one side of the target framing element 182 is coupled to the switch actuator finger 179, which is spring loaded. The target framing element 182 is biased toward the extended position, but closes the switch 178 circuit as it is pushed toward the distal end of the housing when the user pushes the applicator 100 against the target skin area. A thermistor 90 may again be mounted on the distal end of the housing 112 to sense the approximate temperature and indicate whether coolant has been jetted from the nozzle when the system is ready to operate.

The double ridged waveguide 160, which is substantially smaller than a regular rectangular waveguide in cross-sectional area, provides a first concentration of electrical field energy, and the reduced height section, which is dielectric filled, not only reduces the area further, but matches the electrical impedance to the skin surface. Consequently, the applicator 100 is easily manipulated, and the flexible input lines, including a flexible input coax line, provide no interference to handling and placement.

In this manner, the surgeon or technician, or other operator, can be immediately ready to target another adjacent location and initiate the timed cycle when the circuits are ready.

The same basic sequence of application cycles is also used in an alternative applicator 200, seen in FIGS. 14–16, which is substantially similar in the manner of operation as to the coolant, pulsed microwave energy delivery, and control system. Thus redundant internal details of this structure are not specifically shown and reference can be made to FIGS. 1–13 for such aspects. These includes the valve actuated coolant system, the sensors and control circuits, the internal wiring, a manually operated control switch and other details which have been omitted for clarity. In the arrangement of FIGS. 14–16, the housing 202 has a relatively low height handle portion 204 tapering down to a distal end 206 of narrower width. The housing 202 contains two side by side double ridged waveguides 210, 212, which may include reduced height distal sections that are dielectric loaded, as in the prior example of FIGS. 7–12, although these are not shown. The waveguides 210, 212 do, however, include angled distal end sections 214, 215, the angle in this example being approximately 600 relative to the principal longitudinal axis of the waveguides 210, 212. The distal end 206 of the housing 202 similarly is angled in a like manner, enabling the applicator 200 to be held in a convenient position, spaced from the body surface of the recipient so that guide markers on an indicia frame or element (which may correspond to that of the examples of FIGS. 1–13) at the end can readily be visualized to enable the target area to be selected.

As an alternative to a manual control switch, as seen in FIGS. 14–16, the distal end 206 of the housing includes a pair of tracking wheels 217, 219 beneath the angled ends of the waveguides 210, 212, the wheels 217, 219 being interconnected by a shaft 220 mounted in the housing distal end 206. A smaller hub enclosing a rotary encoder element 222 generates an electrical signal or a mechanical impulse whenever the tracking wheels 217, 219 go through a selected angular increment. The rotary encoder element 222 may be an optical encoder or a mechanical device with detent surfaces, to provide impulses to a switch 224 at the successive increments. The angular increments are chosen to correspond in linear distance to the height of the emitter apertures in the waveguides 214, 215 at the distal end 206, and the switch 224 provides a signal to the control circuits, as in the example of FIGS. 1–6, to repeat the firing procedure. That is, when the applicator is ready to trigger and the proper position is reached, the flow of coolant is initiated, a thermistor detects the level of satisfactory cooling, and the microwave source is pulsed for the selected duration.

In this example, however, the two waveguides 210, 212, are operated alternately. For this purpose, an input coax line 230 feeds into a central input of a single pole double throw RF switch 234, which has two coax outputs 236, 237 feeding to SMA connectors 240, 241 each coupling into a different double ridged waveguide 210 or 212 and providing a coax to rectangular waveguide transition. Signals from the control circuits (see FIG. 1) alternate the input microwave energy between the two ridged waveguides 210, 212 as operation proceeds through successive positions.

The tracking wheel arrangement thus provides measurements and control signals as the applicator 200 is moved between positions. Once pulses have been emitted from the two emitter apertures at a given selected location, the applicator 200 is simply rolled along the skin surface a distance measured by the tracking wheel combination. Without raising the applicator 200 off the skin surface, the operator is informed by an indicator light, a distinct sound, or even a tactile impression, such as a vibration, that the precisely determined next location has been reached. In this manner, while also firing microwave pulses alternately from the two adjacent emitters, the operating doctor or technician can proceed immediately between successive positions, and total application time can be significantly reduced.

While there has been described above and illustrated in the drawings various forms and modifications in accordance with the invention, it will be appreciated that the invention is not limited thereto but encompasses all variations and alternatives in accordance with the appended claims.

We claim:

1. A handheld applicator for directing a dosage of microwave energy to an epidermal surface for a therapeutic purpose while receiving microwave energy and a coolant, comprising:
   a housing configured to be held in one hand and pointed with a distal end toward the epidermal surface, the distal end including means configured to define a distal spacer gap;
   waveguide means within the housing and extending in a distal direction toward a distal end, the distal end of the waveguide means defining an emitter opening distanced from the epidermal contacting surface by the distal spacer gap when the distal end of the housing is in contact with the epidermal surface;
   coolant delivery means disposed within the housing and extending adjacent one side of the emitter opening in communication with the spacer gap;
   temperature sensing means disposed adjacent the opposite side of the emitter opening in communication with the spacer gap;
   operator controllable switch means for preliminarily initiating applicator operation;
   means for actuating the coolant delivery means in response to the preliminary initiation; and
   means responsive to the temperature sensing means for commencing delivery of microwave energy after the delivery of coolant is sensed.

2. An applicator in accordance with claim 1 wherein the waveguide means comprises an internally ridged waveguide structure and the coolant delivery means comprises means for delivering pressurized gas at the spacer gap.

3. An applicator in accordance with claim 2, further including liquid responsive means in the coolant delivery means for signaling the presence of liquid in the refrigerant, and wherein the applicator includes flexible microwave energy and coolant supply lines coupled to the posterior end thereof.

4. An applicator in accordance with claim 1, wherein the applicator includes a disposable spacer element removably attachable to the waveguide means at the distal end thereof, the spacer element defining an inner volume open to a predetermined target area of the epidermal surface, and the coolant delivery means directs coolant across the target area at the inner volume.

5. An applicator in accordance with claim 4, wherein the spacer element includes an interior opening spaced from the coolant delivery means, and a deflector for directing coolant passing through the interior opening away from the epidermal surface.

6. An applicator in accordance with claim 1 wherein the applicator further includes means responsive to movement along the epidermal surface for measuring distance traveled, means providing at least two adjacent emitters, and means for alternating delivery of microwave energy from the emitters at each target location.

7. An applicator in accordance with claim 1, wherein the housing comprises a base portion curving into a distal portion configured for convenient retention between the thumb and forefingers, and wherein the applicator includes microwave energy and coolant feed means within the housing curving from the base portion into the distal portion.

8. An applicator in accordance with claim 7, including an indicia bearing element that is axially movably mounted on the distal end of the applicator and providing a spacer gap when firmly engaged against the epidermal surface, and switch means responsive to the axial position of the indicia bearing movable element.

9. A handheld applicator for directing an areally limited dosage of microwave energy from a pulse source to an epidermal surface for therapeutic purposes, and cooling the epidermal surface with a cooling medium from a pressurized source, comprising:
   at least one ridged waveguide structure having a proximal section coupled to receive microwave energy from the pulse source, and a distal section having a distal end of reduced cross-sectional area relative to the at least one ridged waveguide, the distal end of the structure terminating in at least one beam emitting aperture;
   at least one signal actuable solenoid controlled valve mounted on the waveguide structure along the proximal section;
   coolant conduit means extending along the waveguide from the proximal end to the distal end through the solenoid controlled valve, the coolant conduit means including an open end directing coolant onto the epidermal surface adjacent the at least one beam emitting aperture;
   an electrical circuit coupled to the solenoid-controlled valve and to the pulse source for providing actuating signals thereto; and
   an insulative housing defining the exterior of the applicator and encompassing the waveguide structure, solenoid controlled valve, and coolant conduit means.

10. An applicator as set forth in claim 9 above, wherein the waveguide structure comprises a single double ridged waveguide, and wherein the housing has a bulbous proximal portion, an elongated portion of narrower cross-section along the distal section of the waveguide structure, and a transition portion smoothly merging the proximal and distal portions of the housing.

11. An applicator as set forth in claim 9 above, wherein the waveguide structure comprises a pair of double ridged waveguides lying in adjacent and parallel relation and extending into the distal portion of the applicator, and the proximal portion of the applicator includes an RF switch coupled to receive microwave energy from the pulse source and applying microwave energy to the separate waveguides at the proximal ends thereof.

12. An applicator as set forth claim 11 above, wherein the waveguides have a principal longitudinal axis along the major portion of their lengths and have distal terminal sections angled in excess of 45° relative to the principal axis.

13. An applicator as set forth in claim 9 above, wherein the applicator includes a measuring member at the distal end thereof for engagement with the epidermal surface toward which energy is emitted, the measuring member being responsive to the movement of the applicator relative to the surface, and the applicator further includes a switch responsive to movement of the member for signaling an incremental change in position.

14. An applicator as set forth in claim 9 above, wherein the applicator further comprises a switch mounted with the housing adjacent the distal end thereof and having an actuator element positioned to be responsive to engagement of the applicator against the epidermal surface for providing an actuating signal responsive thereto to the electrical circuit.

15. An applicator as set forth in claim 14 above, wherein the applicator further comprises temperature sensing means including a thermistor adjacent the emitting aperture responsive to flow of coolant for providing a signal to the electrical circuits that coolant has been directed onto the epidermal surface.

16. An applicator as set forth in claim 9 above, wherein the applicator further comprises a guide member at the distal end, interposed between the emitter aperture and the epidermal surface, the guide member including indicia visible to an operator and adjacent the distal end of the housing and demarcating the emitter aperture position, the guide member being configured to be in non-interfering relation to emitted microwaves.

17. A handheld applicator for use by an operator in directing microwave energy pulses of selected power and duration distally toward a target area of the skin of a patient as a coolant gas is supplied from an associated system, comprising:
    an exterior housing including a base and angled distal portion configured to define a pencil-style grip for an operator, the housing extending about a longitudinal axis, the base including a coolant conduit, microwave waveguide, and electrical signal connectors in a proximal end thereof, and the housing distal portion including a distal end for location at a target area;
    a microwave waveguide structure disposed within the base along the longitudinal axis, and extending in the distal direction therefrom, the waveguide structure including an extended waveguide disposed from the base to adjacent the distal end, and a distal transition region including a dielectric providing an impedance match to the skin, and the transition region terminating in a transmitting aperture at the distal end of the housing;
    a coolant line within the housing coupled to the coolant line connector, and longitudinally along to the distal end of the housing, the coolant line including a solenoid-controlled valve coupling the first and second coolant lines;
    an operator controllable switch disposed on the housing in position for actuation by the operator for initiating a cycle of operation using both coolant and microwave energy; and
    control circuits for triggering a microwave pulse after ascertaining that coolant has been delivered.

18. An applicator in accordance with claim 17, further including an end cap member removably attachable to the distal end of the waveguide structure and sized to maintain a selected distance between the transmitting aperture and the target area, the end cap member including an interior volume open to the target area for confining coolant flow.

19. An applicator in accordance with claim 18 above, wherein the applicator provides sensing signals to and receives actuating signals from the associated system, and further including delivery nozzle means coupled to the coolant line and directing coolant flow at the distal end of the housing toward the target area, and temperature sensing means spaced apart from the nozzle means at the distal end of the housing providing a temperature signal to the system in response to a predetermined coolant threshold to initiate the microwave pulse triggering.

20. An applicator as set forth in claim 19 above, wherein the coolant nozzle and temperature sensing element are disposed on opposite sides of the target area, and wherein the end cap element includes an egress port for coolant adjacent the temperature sensing element, a deflector element adjacent the egress port for deflecting egressing coolant away from the skin, and a protruding element demarcating a known location of the transmitting aperture.

21. An applicator as set forth in claim 17 above, wherein the housing comprises generally rounded base and distal portion diverging at an angle of less than 90°, the distal portion being of smaller cross-section than the base portion and wherein the switch is disposed on the housing on a top surface of the distal portion such as to be readily accessible to a forefinger of the operator, and wherein the housing includes indicator lights on the top surface of the base.

22. An applicator as set forth in claim 17 above, wherein the coolant is a pressurized gas refrigerant and the applicator further includes a liquid detector in the first coolant line.

23. A cooling device for an irradiating system that directs electromagnetic wave energy toward a target area of a body surface from an emitter having a terminal aperture, comprising:
    a housing coupled to the irradiating system and configured with side walls which encompass the emitter at the terminal aperture, the housing having an open end face coextensive with the emitter aperture, and framing a wave energy impingement area on the body surface that opposes the emitter aperture, the housing side walls defining when the end face is in engagement with the body surface, a predetermined gap between the emitter aperture and the body surface to establish a limited volume adjacent the target area of the body surface;
    the housing further including an outlet port at one of the side walls in communication with the limited volume; and
    a gas nozzle positioned on the opposite side of the emitter aperture from the outlet port for directing coolant gas into the limited volume to flow across the target area of the body surface to the outlet port.

24. A device as set forth in claim 23 above, wherein the housing is removably attachable to the emitter and the outlet port is configured to include a curved wall extending away from the body surface and defining a vent aperture directing exiting coolant gas away from the body surface.

25. A device as set forth in claim 24 above, including in addition at least two indicia members extending outwardly from the housing to demarcate the position of the emitter aperture relative to a target area.

26. The method of exposing a limited target area of a body surface to a source of electronmagnetic wave radiation to effect a histologic change at or beneath the surface with reduced discomfort due to surface heating comprising the steps of:
    establishing a limited volume around the target area of the body surface, the limited volume enclosing the target area except for a side vent path, and having a predetermined height relative to the body surface;
    directing an expanding pressurized refrigerant gas across the body surface within the limited area and toward the side vent to cool the body surface target area by convection;
    sensing the establishment of a temperature in the region of the side vent that is below a selected threshold; and
    initiating application of a pulse of electromagnetic wave radiation toward the target area when the selected temperature threshold is sensed.

27. The method as set forth in claim 26 above, wherein the gas lowers the body surface target area in the range of 10–25° C. and when the wave radiation is microwave radiation in the range of 2 to 20 GHz.

28. The method as set forth in claim 27 above, wherein the body surface temperature in the target area is lowered about 12° C. wherein the microwave radiation is about 24–25 joules/cm$^2$ for about 25–30 MS, and wherein the refrigerant is 1,1,1,2 tetraflourethane.

* * * * *